United States Patent [19]

Beeley et al.

[11] Patent Number: 5,550,137

[45] Date of Patent: Aug. 27, 1996

[54] PHENYLAMINOCARBONYL DERIVATIVES

[75] Inventors: Nigel R. A. Beeley, Thames; Thomas A. Millican, Maidenhead, both of United Kingdom

[73] Assignee: Celltech Therapeutics Limited, Berkshire, United Kingdom

[21] Appl. No.: 77,284

[22] Filed: Jun. 14, 1993

[30] Foreign Application Priority Data

Jun. 15, 1992 [GB] United Kingdom ............... 9212673

[51] Int. Cl.$^6$ .................. A61K 31/44; C07D 213/30
[52] U.S. Cl. ................ 514/354; 514/357; 546/323; 546/337; 564/166
[58] Field of Search .................. 546/323, 337; 514/354, 357

[56] References Cited

FOREIGN PATENT DOCUMENTS

| | | |
|---|---|---|
| 0497564 | 8/1992 | European Pat. Off. . |
| WO92/12961 | 8/1992 | WIPO . |
| WO94/02465 | 2/1994 | WIPO . |

OTHER PUBLICATIONS

Ashton et al., "Selective Type IV Phosphodiesterase Inhibitors as Antiasthmatic Agents. The Syntheses and Biological Activities of 3–(Cyclopentyloxy)–4–methoxybenzamides and Analogues", Amer. Chem. Soc. 37(11):1696–1703 (1994).

Chemical Abstracts 99(6): 43556Z "Hypoglycemic Pharmaceuticals Containing Manzammide Derivatives" (1983).

Chemical Abstracts, 108(15): 131583P "Preparation of N–Pyridyl–4 (Benzyloky) Benzamides as Cardiotonics" (1988).

Chemical Abstracts, 98: 125577y, 1982.

Grammaticakis, P., "Contribution A L'Etude de L'Absortion Dans L'Ultraviolet Moyen Et Le Visible Des N–Aroyl–Arylamines IV", Bulletin DeLa Societa Chemique De France pp. 848–858 (1965).

Manhas, et al., "Heterocyclic Compounds XII Quinazoline Derivatives as Potential Antifertility Agents (1)", J. Heteroxyxlic Chem. 16:711–715 (1979).

Mathison et al. "Synthesis and Hypotensive Properties of Tetrahydroixoquinolines", J. Med. Chem. 16(4):332–336 (1973).

Tsutsumi et al. CA 113: 6599a, 1990.

Sakakibara et al. CA 108: 131583p, 1988.

*Primary Examiner*—Jane Fan
*Attorney, Agent, or Firm*—Woodcock Washburn Kurtz Mackiewicz & Norris

[57] ABSTRACT

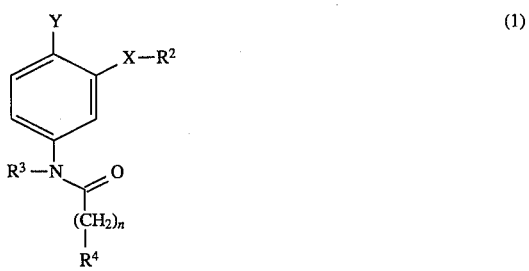

(1)

Compounds of formula (1) are described wherein Y represents a halogen atom or a group —OR$^1$ where R$^1$ represents an optionally substituted alkyl group; R$^2$ represents an optionally substituted cycloalkyl, cycloalkenyl or polycycloalkyl group; R$^3$ represents a hydrogen atom or an alkyl, aryl or aralkyl group; R$^4$ represents an aryl or heteroaryl group; X represents —O—, —S—, —CH$_2$— or —N(R$^5$)—, where R$^5$ is a hydrogen atom or an alkyl group; n is zero or an integer or value 1, 2 or 3; and the salts, solvates and hydrates thereof. The compounds are selective phosphodiesterase IV inhibitors and are useful for the prophylaxis or treatment of inflammatory diseases.

16 Claims, No Drawings

PHENYLAMINOCARBONYL DERIVATIVES

FIELD OF THE INVENTION

This invention relates to a novel series of phenylaminocarbonyl derivatives, to processes for their preparation, to pharmaceutical compositions containing them, and to their use in medicine.

BACKGROUND TO THE INVENTION

Many hormones and neurotransmitters modulate tissue function by elevating intra-cellular levels of adenosine 3', 5'-cyclic monophosphate (cAMP). The cellular levels of cAMP are regulated by mechanisms which control synthesis and breakdown. The synthesis of cAMP is controlled by adenylyl cyclase which may be directly activated by agents such as forskolin or indirectly activated by the binding of specific agonists to cell surface receptors which are coupled to adenylyl cyclase. The breakdown of cAMP is controlled by a family of phosphodiesterase (PDE) isoenzymes, which also control the breakdown of guanosine 3',5'-cyclic monophosphate (cGMP). To date, seven members of the family have been described (PDE I–VII) the distribution of which varies from tissue to tissue. This suggests that specific inhibitors of PDE isoenzymes could achieve differential elevation of cAMP in different tissues, [for reviews of PDE distribution, structure, function and regulation, see Beavo & Reifsnyder (1990) TIPS, 11:150– 155 and Nicholson et al (1991) TIPS, 12:19–27].

There is clear evidence that elevation of cAMP in inflammatory leukocytes leads to inhibition of their activation. Furthermore, elevation of cAMP in airway smooth muscle has a spasmolytic effect. In these tissues, PDE IV plays a major role in the hydrolysis of cAMP. It can be expected, therefore, that selective inhibitors of PDE IV would have therapeutic effects in inflammatory diseases such as asthma, by achieving both anti-inflammatory and bronchodilator effects.

The design of PDE IV inhibitors has met with limited success to date, in that many of the potential PDE IV inhibitors which have been synthesised have lacked potency and/or have been capable of inhibiting more than one type of PDE isoenzyme in a non-selective manner. Lack of a selective action has been a particular problem given the widespread role of cAMP in vivo and what is needed are potent selective PDE IV inhibitors with an inhibitory action against PDE IV and little or no action against other PDE isoenzymes.

SUMMARY OF THE INVENTION

We have now found a novel series of phenylaminocarbonyl derivatives, members of which are potent inhibitors of PDE IV at concentrations at which they have little or no inhibitory action on other PDE isoenzymes. These compounds inhibit the isolated PDE IV enzyme and also elevate cAMP in isolated leukocytes. Certain compounds prevent inflammation in the lungs induced by carrageenan, platelet-activating factor (PAF), interleukin-5 (IL-5) or antigen challenge. These compounds also suppress the hyperresponsiveness of airway smooth muscle seen in inflamed lungs. The compounds of the invention are therefore of use in medicine, especially in the prophylaxis and treatment of asthma.

Thus according to one aspect of the invention, we provide a compound of formula (1)

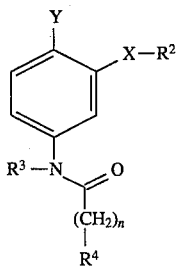

wherein

Y is a halogen atom or a group —OR$^1$ where R$^1$ is an optionally substituted alkyl group;

R$^2$ is an optionally substituted cycloalkyl, cycloalkenyl or polycycloalkyl group;

R$^3$ is a hydrogen atom or an alkyl, aryl or aralkyl group;

R$^4$ is an aryl or heteroaryl group;

X is —O—, —S— —CH$_2$— or —N(R$^5$)13 , where R$^5$ is a hydrogen atom or an alkyl group;

n is zero or an integer of value 1, 2 or 3; and the salts, solvates and hydrates thereof.

In the compounds of formula (1), when Y is a halogen atom it may be for example a fluorine, chlorine, bromine or iodine atom.

When Y in the compounds of formula (1) is a group OR$^1$, R$^1$ may be, for example, an optionally substituted straight or branched alkyl group, for example, a C$_{1-6}$ alkyl group, e.g. a C$_{1-3}$ alkyl group, such as a methyl, ethyl, n-propyl, i-propyl, n-butyl, i-butyl, s-butyl, t-butyl, n-pentyl, i-pentyl or n-hexyl group. Optional substituents which may be present on R$^1$ groups include one or more halogen atoms, e.g. fluorine, chlorine, bromine or iodine atoms.

When R$^2$ in the compounds of formula (1) is an optionally substituted cycloalkyl or cycloalkenyl group it may be for example a C$_{3-8}$ cycloalkyl group such as a cyclobutyl, cyclopentyl or cyclohexyl group or a C$_{3-8}$ cycloalkenyl group such as a cyclobutenyl, cyclopentenyl or cyclohexenyl group, each cycloalkyl or cycloalkenyl group being optionally substituted by one, two or three substituents selected from halogen atoms, e.g. fluorine, chlorine, bromine or iodine atoms, C$_{1-6}$ alkyl e.g. C$_{1-3}$ alkyl such as methyl or ethyl, hydroxyl or C$_{1-6}$ alkoxy e.g. C$_{1-3}$ alkoxy such as methoxy or ethoxy groups. Polycycloalkyl groups represented by the group R$^2$ include optionally substituted C$_{7-10}$ polycycloalkyl groups e.g. C$_{7-10}$ bicycloalkyl or C$_{7-10}$ tricycloalkyl groups such as bicyclo[2.2.1] heptyl or indanyl groups optionally substituted by one, two or three substituents as just described for substituted cycloalkyl or cycloalkenyl groups represented by R$^2$.

The group R$^3$ in the compounds of formula (1) may be a hydrogen atom or a straight or branched C$_{1-6}$ alkyl group, e.g. a C$_{1-3}$ alkyl group. Particular groups include methyl, ethyl, n-propyl, i-propyl, n-butyl, i-butyl, s-butyl, or t-butyl groups. Alternatively, R$^3$ may represent a C$_{6-12}$ aryl group such as an optionally substituted phenyl group or a C$_{6-12}$ aryl C$_{1-6}$ alkyl group, e.g. an optionally substituted phenylC$_{1-3}$alkyl group such as an optionally substituted benzyl or phenethyl group.

When the group R$^4$ in compounds of formula (1) is an aryl group, it may be an optionally substituted C$_{6-12}$ aryl group such as an optionally substituted phenyl or 1- or 2-naphthyl group. Heteroaryl groups represented by R$^4$ include optionally substituted C$_{3-6}$ heteroaryl groups containing for example one or two heteroatoms selected from —O— or —S— or groups —N($R^5$)— [where $R^5$ is as defined above], such as pyrrolyl, furanyl, oxazolyl, thiazolyl, pyrazoyl, pyridinyl or pyrimidinyl groups. The heteroaryl group may be attached to the remainder of the molecule of formula (1) through any ring carbon or heteroatom as desired.

The aryl or heteroaryl groups represented by $R^3$ and $R^4$ in compounds of formula (1) may each optionally be substituted by one, two or more substituents ($R^6$) selected from halogen atoms, e.g. fluorine, chlorine, bromine or iodine atoms, or $C_{1-6}$ alkyl, e.g. methyl or ethyl, $C_{1-6}$ alkoxy, e.g. methoxy or ethoxy, $C_{2-6}$ alkylenedioxy, e.g. ethylenedioxy, $C_{5-7}$ cycloalkoxy, e.g. cyclopentyoxy, halo$C_{1-6}$ alkyl, e.g. tri-fluoromethyl, $C_{1-6}$ alkylamino, e.g. methylamino or ethylamino, $C_{1-6}$ dialkylamino, e.g. dimethylamino or diethylamino, amino ($NH_2$), nitro, cyano, hydroxyl (OH), carboxyl ($CO_2H$), —$CO_2R^7$ [where $R^7$ is a $C_{1-6}$ alkyl e.g. methyl or ethyl, $C_{6-12}$ aryl$C_{1-3}$ alkyl, e.g. benzyl or phenethyl or $C_{6-12}$ aryl, e.g. phenyl group], $C_{1-6}$ alkanoyl e.g. acetyl, sulphonyl (—$SO_3H$), $C_{1-6}$ alkylsulphonyl, e.g. methylsulphonyl, aminosulphonyl (—$SO_2NH_2$), $C_{1-6}$ alkylaminosulphonyl e.g. methylaminosulphonyl or ethylaminosulphonyl, $C_{1-6}$ dialkylaminosulphonyl, e.g. dimethylaminosulphonyl or diethylaminosulphonyl, carboxamido (—$CONH_2$), $C_{1-6}$ alkylaminocarbonyl, e.g. methylaminocarbonyl or ethylaminocarbonyl, $C_{1-6}$ dialkylaminocarbonyl, e.g. dimethylaminocarbonyl or diethylaminocarbonyl, sulphonylamino (—$NHSO_2H$), $C_{1-6}$ alkylsulphonylamino, e.g. methylsulphonylamino or ethylsulphonylamino, $C_{1-6}$ dialkylsulphonylamino, e.g. dimethylsulphonylamino or diethylsulphonylamino groups, —$NHCOR^8$ (where $R^8$ is a $C^{1-6}$ alkyl group, e.g. a methyl, ethyl, n-propyl, or i-propyl group, or an aryl, e.g. phenyl or aryl $C_{1-3}$ alkyl, e.g. benzyl, or phenethyl group), —$NHCSR^8$, —$NHCONH_2$, —$NHCONHR^7$, —$NHCON(R^7)$ (where each $R^7$ group is the same or different), or $C_{1-6}$alkanoylamino$C_{1-6}$alkyl, e.g. acetylaminomethyl groups.

It will be appreciated that where two or more $R^6$ substitutents are present, these need not necessarily be the same atom and/or groups. The $R^6$ substituents may be present at any ring carbon atom away from the atom attached to the rest of the molecule of formula (1). Thus for example, in substituted phenyl groups represented by $R^3$ or $R^4$ any substituent(s) may be present at the 2-; 3-; 4-; 5-; 6-; 2,6-; 2,3- or 2,4- positions relative to the ring carbon atom attached to the remainder of the molecule. In another example, when the group $R^4$ is a heteroaryl group any carbon atom not attached to the remainder of the molecule may be substituted. One, two or more carbon atoms may have substituents. Thus, in one example, when $R^4$ is a substituted 4-pyridinyl group any substituent(s) may be present at the 2-; 3-; 5-; 6-; 2,5- or 3,5 positions relative to the nitrogen atom.

When the group —N($R^5$)— is present in the compounds of formula (1), $R^5$ may be a hydrogen atom or a $C_{1-6}$ alkyl group such as a methyl or ethyl group.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, p-toluenesulphonates, phosphates, sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

One particular group of compounds according to the invention has the formula (1) wherein Y is an —$OR^1$ group, $R^2$ is an optionally substituted cycloalkyl or polycycloalkyl group and $R^1$, $R^3$, $R^4$, X and n are as defined for formula (1) and the salts, solvates and hydrates thereof.

In the compounds of formula (1), the group Y is preferably an —$OR^1$ group. Particularly useful compounds of this type are those where $R^1$ is an optionally substituted $C_{1-3}$ alkyl group, particularly an ethyl group, or especially a methyl group.

The group X in compounds of formula (1) is preferably —O—.

$R^2$ in compounds of formula (1) is preferably an optionally substituted cyclopentyl group.

n in the compounds of formula (1) is preferably zero or an integer of value 1.

A useful group of compounds according to the invention has the formula (1) wherein Y is a group —$OR^1$ where $R^1$ is an optionally substituted straight or branched $C_{1-3}$ alkyl group, $R^2$ is an optionally substituted $C_{3-8}$-cycloalkyl group, $R^3$ is a hydrogen atom, $R^4$ is a $C_{6-12}$aryl or $C_{3-6}$-heteroaryl group, X is —O—, n is zero or an integer of value 1 and the salts, solvates and hydrates thereof. In compounds of this type, n is, in particular, zero.

A particularly useful group of compounds of formula (1) has the formula (2):

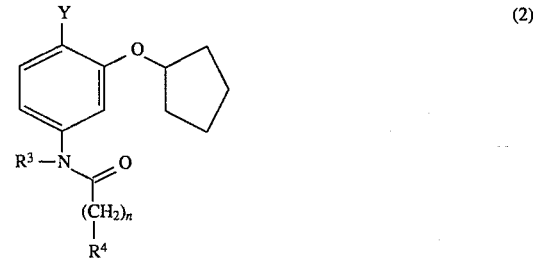

(2)

and the salts, solvates and hydrates thereof, wherein n, $R^3$ and $R^4$ are as defined for formula (1).

Particular compounds of formula (2) are those wherein n is an integer of value 1, or, especially, is zero.

In the compounds of formulae (1) and (2), $R^3$ is preferably a hydrogen atom.

$R^4$ in the compounds of formulae (1) and (2) is preferably an optionally substituted phenyl, or an optionally substituted 2-,3- or, especially, 4-pyridinyl group. Particularly useful substituents include halogen atoms such as fluorine, chlorine, or bromine atoms, and groups selected from nitro, trifluoromethyl, carboxamido, —$CO_2CH_3$, —$CH_3$, or —$OCH_3$.

Particularly useful compounds according to the invention are:

3-Cyclopentyloxy-4-methyloxy-N-(2-Nitrobenzoyl)aniline; N-(3-Cyclopentyloxy-4-methyloxyphenyl)-4-pyridinecarboxamide; 3-Cyclopentyloxy-4-methyloxy-N-(3-Nitrobenzoyl)aniline; N-(3-Cyclopentyloxy-4-methyloxyphenyl)-1,2-benzenedicarboxamide; N-Benzoyl-3-cyclopentyloxy-4-methyloxyaniline; Methyl 2-[N-3-(Cyclopentyloxy-4-methyloxyphenyl)carbamoyl]benzoate; N-(3-Cyclopentyloxy-4-methyloxyphenyl)-3,5-dichloro-4-pyridinecarboxamide; and the salts, solvates and hydrates thereof.

Compounds according to the invention are selective and potent inhibitors of PDE IV. The ability of the compounds to act in this way may be simply determined by the tests described in the Examples hereinafter.

The compounds according to the invention are thus of particular use in the prophylaxis and treatment of human diseases where an unwanted inflammatory response or muscular spasm is present and where the elevation of cAMP levels may be expected to prevent or alleviate the inflammation and relax the muscle.

Particular uses to which the compounds of the invention may be put include the prophylaxis and treatment of asthma, especially inflamed lung associated with asthma, or in the treatment of inflammatory airway disease, chronic bronchitis, eosinophilic granuloma, psoriasis and other benign and malignant proliferative skin diseases, endotoxic shock, septic shock, ulcerative colitis, Crohn's disease, reperfusion injury of the myocardium and brain, chronic glomerulonephritis, atopic dermatitis, urticaria, allergic rhinitis, adult respiratory distress syndrome, diabetes insipidus, allergic conjunctivitis and vernal conjunctivitis.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Compounds according to the invention may also elevate cAMP in lymphocytes and thereby suppress unwanted lymphocyte activation in immune-based diseases such as rheumatoid arthritis, transplant rejection and graft versus host disease.

Pharmaceutical compositions according to the invention may take a form suitable for oral, buccal, parenteral or nasal administration, or a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of formula (1) may be formulated for parenteral administration by injection e.g. by bolus injection or continuous infusion. Formulations for injection may be presented in unit dosage form. The compositions for injection may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas.

The compositions may, if desired, be presented in a pack or dispenser device which may contain one or more unit dosage forms containing the active ingredient. The pack or dispense device may be accompanied by instructions for administration.

The quantity of a compound of the invention required for the prophylaxis or treatment of a particular inflammatory condition will vary depending on the compound chosen, and the condition of the patient to be treated. In general, however, daily dosages may range from around 0.01 mg/kg to 100 mg/kg, e.g. around 1 mg/kg to 40 mg/kg body weight for oral or buccal administration from around 0.001 mg/kg to 50 mg/kg body weight for parenteral administration, and around 5 mg to around 1000 mg for nasal administration or administration by inhalation or insufflation.

The compounds according to the invention may be prepared by the following processes. The symbols Y, $R^2$, $R^3$, $R^4$ and X when used in the formulae below are to be understood to represent those groups described above in relation to formula (1) unless otherwise indicated. Thus according to another aspect of the invention, a compound of formula (1) may be prepared by coupling an amine of formula (3):

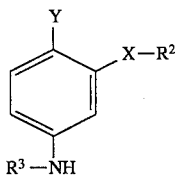

with an acid $R_4(CH_2)_nCO_2H$ or an active derivative thereof. Active derivatives of acids $R_4(CH_2)_nCO_2H$ include, for example, acid anhydrides, or acid halides, such as acid chlorides.

The coupling reaction may be performed using standard conditions for reactions of this type. Thus for example, the reaction may be carried out in a solvent, for example an inert organic solvent such as an ether, e.g. a cyclic ether such as tetrahydrofuran, an amide, e.g. a substituted amide such as dimethylformamide, or a halogenated hydrocarbon such as dichloromethane, at a low temperature, e.g. $-30°$ C. to ambient temperature such as $-20°$ C. to $0°$ C., optionally in the presence of a base, e.g. an organic base such as an amine, e.g. triethylamine or a cyclic amine such as N-methylmorpholine. Where an acid $R_4(CH_2)_nCO_2H$ is used, the reaction may additionally be performed in the presence of a condensing agent, for example a diimide such as N, N'-dicyclohexylcarbodiimide, advantageously in the presence of a triazole such as 1-hydroxybenzotriazole. Alternatively, the acid $R^4(CH_2)_nCO_2H$ may be reacted with a chloroformate, for example ethylchloroformate, prior to reaction with the amine of formula (3).

Intermediate amines of formula (3) in which $R^3$ is a hydrogen atom may be prepared by hydrogenation of a corresponding nitro compound of formula (4):

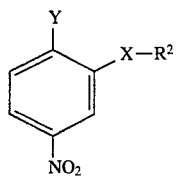

(4)

using for example hydrogen and a metal such as palladium or platinum optionally on a support such as carbon, in a solvent such as an alcohol e.g. methanol or ethanol, preferably at an elevated pressure and temperature Intermediates of formula (3) wherein $R^3$ is as defined above other than a hydrogen atom may be prepared by reaction of a compound of formula (3) where $R^3$ is a hydrogen atom with an appropriate halide $R^3$Hal [where Hal is a halogen atom such as a chlorine, bromine or iodine atom] in the presence of a base such as sodium hydride or an alkoxide such as sodium ethoxide, in a solvent such as an alcohol e.g. ethanol, at ambient temperature or above e.g. around 40° C. or 50° C.

Intermediates of formula (4) in which X is —O—, —S— or —N($R^5$)— may be prepared by alkylation of a corresponding compound of formula (5):

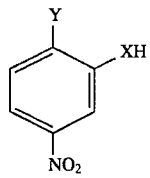

(5)

using a reagent $R^2$Hal [where Hal is as just defined]. The reaction conditions may be those just described for the alkylation of intemediates of formula (3), or, alternatively, where for example the group X is —O— a base such as an alkali metal hydroxide or carbonate, e.g. cesium carbonate may be used in an inert solvent such dimethylformamide at ambient temperature.

Intermediates of formula (4) in which X is —$CH_2$—, may be prepared by reaction of a compound of formula (6)

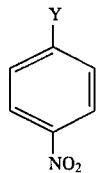

(6)

with an acid halide $R^2$COHal in the presence of a catalyst such as aluminium chloride followed by reduction using zinc and an inorganic acid such as hydrochloric acid, or hydrazine and a base such as an alkali metal hydroxide, e.g. sodium hydroxide.

Intermediates of formulae (5) and (6) and the reagents $R^4(CH_2)_nCO_2H$ and $R^4$Hal are either known compounds or may be prepared from known starting materials by methods analogous to those used for the preparation of the known compounds.

Salts of compounds of formula (1) may be prepared by reaction with an appropriate acid or base in a suitable solvent using conventional procedures.

DESCRIPTION OF SPECIFIC EMBODIMENTS

The following Examples illustrate the invention.

INTERMEDIATE I

3-Cyclopentyloxy-4-methyloxy-1-nitrobenzene

2-Methyloxy-5-nitrophenol (14.27 g, 84.4 mmol) was dissolved in dry dimethylformamide (80 ml). Cyclopentylbromide (176 g, 127 ml, 118.2 mmol) and cesium carbonate (38.5 g, 118.2 mmol) were added and the suspension stirred overnight at room temperature. The mixture was poured into saturated $Na_2CO_3$ (200 ml) and extracted with ethyl acetate (700 ml). The organic layer was washed with saturated $Na_2CO_3$ until no yellow colour was detected. The organic layer was then dried ($MgSO_4$) and concentrated in vacuo to give the title Compound as a yellow solid (15.0 g).

$^1$H NMR δ ($CDCl_3$) 7.85 (1H, dd), 7.72 (1H, d), 6.90 (1H, d), 4.82–4.92 (1H, m), 3.92 (3H, s), 1.60–2.10 (8H, m).

INTERMEDIATE 2

3-Cyclopentyloxy-4-methyloxyaniline

Intermediate 1 was dissolved in degassed methanol and 10% Pd/C (450 mg) was added. The mixture was stirred under $H_2$ gas at room temperature overnight. The catalyst was removed by filtration and the methanol concentrated in vacuo to give the title compound as a dark oil (4.3 g).

$^1$H NMR δ ($CDCl_3$) 6.70 (1H, d), 6.27 (1H, d), 6.20 (1H, dd), 4.68–4.78 ( 1H, m), 3.75 (3H, s), 3.42 (1H, br s), 1.50–1.95 (8H, m).

EXAMPLE 1

N-Benzoyl-3-cyclopentyloxy-4-methyloxyaniline

To an ice cooled solution of Intermediate 2 (20 g, 9.66 mmol) in anhydrous pyridine (20 ml) was added benzoyl chloride dropwise (2.04 g, 1.68 ml, 14.5 mmol) followed by N,N-dimethylaminopyridine (5 mg). The reaction mixture was stirred at room temperature for 3 hours, poured into 1.0M HCl (100 ml) and extracted with ethyl acetate. The ethyl acetate layer was washed with 1.0M HCl (2×50 ml) and dried over $MgSO_4$. Concentration in vacuo gave a brownish oil which was recrystallised twice from $CH_2Cl_2$/hexane to give the title compound as a white solid (1.0 g).

$^1$H NMR δ ($CDCl_3$) 7.80–7.95 (3H, m), 7.40–7.55 (4H, m), 6.98 (1H, dd),6.82 (1H, d), 4.72–4.82 (1H, m), 3.83 (3H, s), 1.50–2.05 (8H, m).

The following compounds were prepared in a similar manner to the compound of Example 1 using Intermediate 2 and the approprirate chloride:

EXAMPLE 2

3-Cyclopentyloxy-4-methyloxy-N-(3-Nitrobenzoyl)aniline $^1$H NMR δ ($CDCl_3$) 8.70 (1H, br s), 8.36 (1H, d), 8.28 (1H, d), 8.20 ( 1H, s), 7.68 (1H, t), 7.41 (1H, s), 7.07 (1H, dd), 6.85 (1H, d), 4.70–4.82 (1H, m), 3.85 (3H, s), 1.50–2.05 (8H, m).

EXAMPLE 3

3-Cyclopentyloxy-4-methyloxy-N-(2-Nitrobenzoyl)aniline $^1$H NMR δ ($CDCl_3$) 8.10 (1H, d), 7.60–7.80 (3H, m), 7.43 (1H, s), 7.35 ( 1H, d), 6.90 (1H, dd), 6.85 (1H, d), 4.75–4.85 (1H, m), 3.87 (3H, s), 1.50–2.05 (8H, m).

EXAMPLE 4

3-Cyclopentyloxy-4-methyloxy-N-(4-Nitrobenzoyl)aniline

¹H NMR δ (CDCl₃) 8.35 (2H, d), 8.02 (2H, d), 7.85 (1H, br s), 7.45 (1H, d), 7.05 (1H, dd), 6.87 (1H, d), 4.75–4.85 (1H, m), 3.87 (3H, s), 1.50–2.05 (8H, m).

EXAMPLE 5

N-(3-Cyclopentyloxy-4-methyloxyphenyl)-2-pyridinecarboxamide

¹H NMR δ (CDCl³) 9.95 (1H, br s), 8.58 (1H, dd), 8.28 (1H, dd), 7.90 (1, m), 7.62 (1H, d), 7.45 (1H, m), 7.12 (1H, dd), 6.88 (1H, d), 4.80–4.90 (1H, m), 3.87 (3H, s), 1.55–2.10 (8H, m).

EXAMPLE 6

N-(3-Cyclopentyloxy-4-methyloxyphenyl)-3-pyridinecarboxamide

¹H NMR δ (CDCl₃) 9.08 (1H, d), 8.78 (1H, dd), 8.20 (1H, dd), 8.05 (1H, br s), 7.35–7.45 (2H, m), 7.02 (1H, dd), 6.85 (1H, d), 4.75–4.85 (1H, m), 3.87 (3H, s), 1.55–2.10 (8H, m).

EXAMPLE 7

N-(3-Cyclopentyloxy-4-methyloxyphenyl)-4-pyridinecarboxamide

¹H NMR δ (CDCl₃) 8.76 (2H, d), 8.0 (1H, br s), 7.70 (2H, d), 7.45 (1H, d),7.05 (1H, dd), 6.85 (1H, d), 4.75–4.85 (1H, m), 3.88 (3H, s), 1.55–2.05( 8H, m).

EXAMPLE 8

N-(3-Cyclopentyloxy-4-methyloxyphenyl)-2-phenylacetamide

¹H NMR δ (CDCl₃) 7.24–7.45 (6H, m), 7.02 (1 H, br s), 6.68–6.80 (2H, m), 4.70–4.80 (1H, m), 3.80 (3H, s), 3.72 (2H, s), 1.55–2.05 (8H, m).

EXAMPLE 9

N-(3-Cyclopentyloxy-4-methyloxyphenyi)-1,2-benzenedicarboxamide

¹H NMR δ (CDCl₃) 8.98 (H, s), 7.60 (1H, dd), 7.48 (1H, dd), 7.35–7.45 (3H, m), 7.05 (1H, dd), 6.78 (2H, br s+d), 5.90 (1H, br s), 4.70–4.80 (1H, m), 3.83 (3H, s), 1.50–2.05 (8H, m).

EXAMPLE 10

Methyl-2-[N-(3-Cyclopentyloxy-4-methyloxyphenyl)carbamoyl]benzoate

¹H NMR δ (CDCl₃) 7.92 (H, d), 7.48–7.65 (4H, m), 7.49 (1H, d), 7.0 (1H, dd), 6.83 (1H, d), 4.75–4.87 (1H, m), 3.88 (3H, s), 3.83 (3H, s), 1.5–2.0 ( 8H, m).

EXAMPLE 11

2-N-(3-Cyclopentyloxy-4-methyloxyphenyl)carbamoyl benzoic acid

¹H NMR δ (CD₃OD) 8.02 (1H, d), 7.50–7.65 (3H, m), 7.37 (1H, dd), 7.10 (1H, dd), 6.87 (1H, d), 4.75–4.85 (1H, m), 3.80 (3H, s), 1.55–2.0 (8H, m).

EXAMPLE 12

N-(3-Cyclopentyloxy-4-methyloxyphenyl)-N-methyl-2-nitrobenzamide

¹H NMR δ (CDCl₃) 8.10 (1H, d), 7.55–7.75 (3H, m), 7.35 (1H, d), 6.98(1H, dd), 6.83 (1H, d), 4.78–4.85 (1H, m), 3.86 (3H, s), 2.7 (3H, s), 1.50–2.05 (8H, m).

EXAMPLE 13

N-(3-Cyclopentyloxy-4-methyloxyphenyl)-3-cyclopentyloxy-4-methyloxybenzamide

¹H NMR δ (CDCl₃) 7.75 (1H, br s), 7.50 (2H, s), 7.38 (1H, dd), 6.8–7.0 (3H, m), 4.75–4.90 (2H, m), 3.90 (3H, s), 3.85 (3H, s), 1.50–2.05 (16H, m).

EXAMPLE 14

N-(3-Cyclopentyloxy-4-methyloxyphenyl)-N-phenyl-4-pyridinecarboxamide

¹H NMR δ (CDCl₃) 8.50 (2H, d, J=6 Hz), 7.27 (2H, d, J=6 Hz), 7.19–7.37 (5H, m), 6.60–6.75 (3H, m), 4.58 (1H, br s), 3.80 (3H, s), 1.62–1.85 (6H, m) 1.50–1.62 (2H, m).

The activity and selectivity of compounds according to the invention was demonstrated in the following tests.

1. Isolated Enzyme

The potency and selectivity of the compounds of the invention was determined using a battery of distinct PDE isoenzymes as follows:

i. PDE I, rabbit heart ii. PDE II, rabbit heart iii. PDE III, rabbit heart iv. PDE IV, HL60 cells.

The enzymes were purified to kinetic homogeneity using standard chromatographic techniques.

Phosphodiesterase activity was assayed as follows. The reaction was conducted in 150 μl of standard mixture containing (final concentrations): 50 mM TES-NaOH buffer (pH 7.5), 10 mM MgCl₂, 0.1 μM [³H]-cAMP and vehicle or various concentrations of the test compounds. The reaction was initiated by addition of enzyme and conducted at 30° C. for between 5 to 30 mins. The reaction was terminated by addition of 50 μl 2% trifluoroacetic acid containing [¹⁴C]-5'AMP for determining recovery of the product. An aliquot of the sample was then applied to a column of neutral alumina and the [³H]-cAMP eluted with 10 ml 0.1 TES-NaOH buffer (pH8). The [³H]-5'-AMP product was eluted with 2 ml 2M NaOH into a scintillation vial containing 10 ml of scintillation cocktail. Recovery of [³H]-5'AMP was determined using the [¹⁴C]-5'AMP and all assays were conducted in the linear range of the reaction.

Compounds according to the invention were able to inhibit the action of the PDE IV HL60 enzyme at concentrations at which they had little or no effect on the action of each of the other PDE isoenzymes. Thus, compounds of the Examples have approximate Ki values (Ki PDE IV HL60 at (1 μM) in the nM-μM range, for example the compounds of Examples 1 and 3 have approximate Ki values of 391 nM and 179 nM respectively.

2. The Elevation of cAMP in Leukocytes

The effect of compounds of the invention on intracellular cAMP was investigated using human neutrophils or guinea pig eosinophils. Human neutrophils were separated from peripheral blood, incubated with dihydrocytochalasin B and the test compound for 10 min and then stimulated with FMLP. Guinea pig eosinophils were harvested by peritoneal lavage of animals previously treated with intra-peritoneal injections of human serum. Eosinophils were separated from the peritoneal exudate and incubated with isoprenaline and test compound. With both cell types, suspensions were centrifuged at the end of the incubation, the cell pellets were resuspended in buffer and boiled for 10 min prior to measurement of cAMP by specific radioimmunoassay (DuPont).

The most potent compounds according to the invention induced a concentration-dependent elevation of cAMP in neutrophils and/or eosinophils at concentrations in the range 1 nM to 1 µM.

3. Suppression of Leukocyte Function

Compounds of the invention were investigated for their effects on superoxide generation and chemotaxis of human neutrophils. Neutrophils were separated from peripheral blood, incubated with dihydrocytochalasin B for superoxide generation only and test compound prior to stimulation with FMLP. The most potent compounds caused a concentration-dependent inhibition of superoxide generation and chemotaxis at concentrations in the range 0.1 nM to 1 µM.

4. Relaxation of Constricted Airway Smooth Muscle in vitro

The effects of compounds of the invention on guinea-pig isolated tracheal smooth muscle were investigated. Isolated tracheal rings were suspended in organ baths and immersed in oxygenated Krebs' solution. The smooth muscle was contracted with sub-maximal concentrations of histamine or carbachol prior to the addition of increasing concentrations of test compound to the organ baths. The most potent compounds caused a concentration-dependent reversal of both histamine and carbachol-induced contractions at concentrations in the range 1 nM to 100 µM. The compounds were generally more potent in reversing histamine-induced tone than carbachol-induced tone.

5. Effects on Cardiac Muscle in vitro

Compounds of the invention have been tested for their effects on isolated cardiac muscle. Right atrial and papillary muscles were dissected out from the hearts of guinea pigs and suspended in organ baths for measuring the rate (chronotropic) of spontaneously beating atria and force (inotropic) of the electrically stimulated papillary muscle. In these preparations, selective PDE IV inhibitors such as rolipram do not have any direct effects whereas selective PDE III inhibitors such as milrinone have positive chronotropic and inotropic effects. The nonspecific PDE inhibitor theophylline, which is used in asthma as a bronchodilator, also causes significant cardiovascular changes such as tachycardia. Selective PDE IV inhibitors have advantage over theophylline, therefore, through reduced cardiovascular side effects. The most potent and selective compounds of the invention had no direct effects on the atrial and papillary muscles in vitro at concentrations up to 100 µM but in combination with PDE III inhibitors, these inhibitors showed an enhancement of chronotropic and inotropic activity, typical of selective type IV inhibitors.

6. Anti-inflammatory Activity in vivo.

Compounds of the invention have been tested in models of experimental pleurisy in the rat induced by carrageenan, platelet-activating factor (PAF), or interleukin-5 (IL-5). The compounds caused a dose-dependent reduction in carrageenan-induced accumulation of inflammatory exudate and total leukocyte numbers at 6 h following oral (1–50 mg/kg), intravenous (0.1–10 mg/kg), or intraperitoneal (0.1–10 mg/kg) administration. Compounds of the invention also reduced PAF or IL-5-induced pleural eosinophilia at 24 h following oral (1–50 mg/kg), intravenous (0.1–10 mg/kg) or intraperitoneal (0.1–10 mg/kg) dosing.

7. Anti-allergic Activity in vivo

Compounds of the invention have been tested for effects on an IgE-mediated allergic pulmonary inflammation induced by inhalation of antigen by sensitised guinea pigs. Guinea pigs were initially sensitised to ovalbumin under mild cyclophosphamide-induced immunosuppression, by intraperitoneal injection of antigen in combinations with aluminium hydroxide and pertussis vaccine. Booster doses of antigen were given two and four weeks later and at six weeks, animals were challenged with aerosolised ovalbumin whilst under cover of an intraperitoneally administered anti-histamine agent (mepyramine). After a further 48 h, bronchial alveolar lavages (BAL) were performed and the numbers of eosinophils and other leukocytes in the BAL fluids were counted. The lungs were also removed for histological examination for inflammatory damage. Administration of compounds of the invention (0.1–10 mg/kg i.p.), up to three times during the 48 h following antigen challenge, lead to a significant reduction in the eosinophilia and the accumulation of other inflammatory leukocytes. There was also less inflammatory damage in the lungs of animals treated with compounds of the invention.

8. Effects on Pulmonary Dynamics

Compounds of the invention have been tested for their effects on ozone-induced hyperreactivity of the airways of guinea pigs. Following the inhalation of ozone, guinea pigs become very much more sensitive to the bronchoconstrictor effects of inhaled histamine than naive animals. There is a pronounced shift to the left (10–30 fold) of the dose response curve to histamine and a highly significant increase in the maximum increase in pulmonary resistance. Compounds of the invention administered 1 h prior to ozone by the intraperitoneal (0.01–1 mg/kg) or oral (0.1–10 mg/kg) route caused a dose-dependent inhibition of ozone-induced hyperreactivity.

We claim:

1. A compound of formula (1)

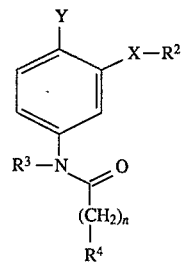

wherein:

Y is a halogen atom or a group —OR$^1$, where R$^1$ is an optionally substituted C$_{1-6}$alkyl group, said R$^1$ substituent being halogen;

R$^2$ is a C$_{3-8}$cycloalkyl, C$_{3-8}$-cycloalkenyl or C$_{7-10}$polycycloalkyl group which is optionally substituted with one to three substituents, said R$^2$ substituents being halogen, C$_{1-6}$alkyl, hydroxyl or C$_{6-12}$alkoxy;

R$^3$ is a hydrogen atom or a C$_{1-6}$alkyl, C$_{6-12}$aryl or C$_{6-12}$arylC$_{1-6}$ group;

R$^4$ is a pyridinyl group which is optionally substituted with one to four substituents, said R$^4$ substituents being halogen, C$_{1-6}$alkyl, C$_{1-6}$alkoxy, C$_{2-6}$alkylenedioxy, C$_{5-7}$cycloalkoxy, haloC$_{1-6}$alkyl, C$_{1-6}$alkylamino, C$_{1-6}$dialkylamino, amino, nitro, cyano, hydroxyl, carboxyl (—CO$_2$H), —CO$_2$R$^7$, C$_{1-6}$alkanoyl, sulphonyl (—SO$_3$H), C$_{1-6}$alkylsulphonyl, aminosulphonyl (—SO$_2$NH$_2$), C$_{1-6}$alkylaminosulphonyl, C$_{1-6}$dialkylaminosulphonyl, carboxamido (—CONH$_2$), C$_{1-6}$alkylaminocarbonyl, C$_{1-6}$dialkylaminocarbonyl, sulphonylamino (—NHSO$_2$H), C$_{1-6}$alkylsulphonylamino, C$_{1-6}$dialkylsulphonylamino, —NHCOR$^8$, —NHCSR$^8$, —NHCONH$_2$, —NHCONHR$^7$, —NHCON(R$^7$)$_2$ or C$_{1-6}$alkanoylaminoC$_{1-6}$alkyl;

each of R$^7$ and R$^8$ is independently C$_{1-6}$alkyl, C$_{6-12}$aryl or C$_{6-12}$arylC$_{1-3}$alkyl;

X is —O—, —S—, —CH$_2$— or —N(R$^5$)—, where R$^5$ is a hydrogen atom or a C$_{1-6}$alkyl group;

n is zero or an integer of value 1, 2 or 3;

or a salt, solvate or hydrate thereof.

2. A compound according to claim 1 wherein Y is an —OR$^1$ group.

3. A compound according to claim I wherein n is zero.

4. A compound of formula (1)

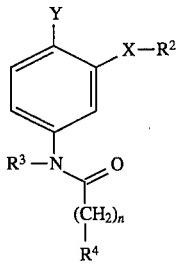

(1)

wherein:

Y is a halogen atom or a group —OR$^1$, where R$^1$ is an optionally substituted straight or branched C$_{1-3}$alkyl group, said R$^1$ substituent being halogen;

R$^2$ is a C$_{3-8}$cycloalkyl group which is optionally substituted with one to three substituents, said R$^2$ substituents being halogen, C$_{1-6}$alkyl, hydroxyl or C$_{1-6}$alkoxy;

R$^3$ is a hydrogen atom;

R$^4$ is a pyridinyl group which is optionally substituted with one to four substituents, said R$^4$ substituents being halogen, C$_{1-6}$alkyl, C$_{1-6}$alkoxy, C$_{2-6}$alkylenedioxy, C$_{5-7}$cycloalkoxy, haloC$_{1-6}$alkyl, C$_{1-6}$alkylamino, C$_{1-6}$dialkylamino, amino, nitro, cyano, hydroxyl, carboxyl (—CO$_2$H), —CO$_2$R$^7$, C$_{1-6}$alkanoyl, sulphonyl (—SO$_3$H), C$_{1-6}$alkylsulphonyl, aminosulphonyl (—SO$_2$NH$_2$), C$_{1-6}$alkylaminosulphonyl, C$_{1-6}$dialkylaminosulphonyl, carboxamido (—CONH$_2$), C$_{1-6}$alkylaminocarbonyl, C$_{1-6}$dialkylaminocarbonyl, sulphonylamino (—NHSO$_2$H), C$_{1-6}$alkylsulphonylamino, C$_{1-6}$dialkylsulphonylamino, —NHCOR$^8$, —NHCSR$^8$, -13 NHCONH$_2$, —NHCONHR$^7$, —NHCON(R$^7$)$_2$ or C$_{1-6}$alkanoylaminoC$_{1-6}$alkyl;

each of R$^7$ and R$^8$ is independently C$_{1-6}$alkyl, C$_{6-12}$aryl or C$_{6-12}$arylC$_{1-3}$alkyl;

X is —O—;

n is zero or an integer of value 1;

or a salt, solvate or hydrate thereof.

5. A compound according to claim 4 wherein R$^2$ is a cyclopentyl group.

6. A compound according to claim 4 wherein n is zero.

7. A compound of formula (2)

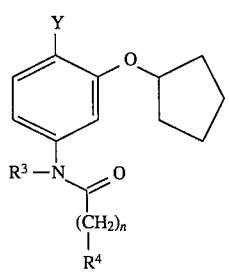

(2)

wherein:

R$^3$ is a hydrogen atom or a C$_{1-6}$alkyl, C$_{6-12}$aryl or C$_{6-12}$arylC$_{1-6}$ group;

R$^4$ is a pyridinyl group which is optionally substituted with one to four substituents, said R$^4$ substituents being halogen, C$_{1-6}$alkyl, C$_{1-6}$alkoxy, C$_{2-6}$alkylenedioxy, C$_{5-7}$cycloalkoxy, haloC$_{1-6}$alkyl, C$_{1-6}$alkylamino, C$_{1-6}$dialkylamino, amino, nitro, cyano, hydroxyl, carboxyl (—CO$_2$H), —CO$_2$R$^7$, C$_{1-6}$alkanoyl, sulphonyl (—SO$_3$H), C$_{1-6}$alkylsulphonyl, aminosulphonyl (—SO$_2$NH$_2$), C$_{1-6}$alkylaminosulphonyl, C$_{1-6}$dialkylaminosulphonyl, carboxamido (—CONH$_2$), C$_{1-6}$alkylaminocarbonyl C$_{1-6}$dialkylaminocarbonyl, sulphonylamino (—NHSO$_2$H), C$_{1-6}$alkylsulphonylamino C$_{1-6}$dialkylsulphonylamino, —NHCSR$^8$, —NHCSR$^8$, —NHCONH$_2$, —NHCONHR$^7$, —NHCON(R$^7$)$_2$ or C$_{1-6}$alkanoylaminoC$_{1-6}$alkyl;

each of R$^7$ and R$^8$ is independently C$_{1-6}$alkyl, C$_{6-12}$aryl or C$_{6-12}$arylC$_{1-3}$alkyl;

n is zero or an integer of value 1, 2 or 3;

or a salt, solvate or hydrate thereof.

8. A compound according to claim 7 wherein R$^3$ is a hydrogen atom.

9. A compound according to claim 7 wherein n is zero or an integer of value 1.

10. A compound according to claim 7 wherein R$^3$ is a hydrogen atom, n is zero and R$^4$ is an optionally substituted pyridinyl group.

11. A compound which is selected from the group consisting of:

N-(3-Cyclopentyloxy-4-methyloxyphenyl)-4-pyridinecarboxamide; and

N-(3-Cyclopentyloxy-4-methyloxyphenyl)-1,2-benzenedicarboxamide; N-Benzoyl-3-cyclopentyloxy-4-methyloxyaniline;

Methyl-2-N-(3-Cyclopentyloxy-4-methyloxyphenyl)-3, 5-dichloro-4-pyridinecarboxamide;

or a salt, solvate or hydrate thereof.

12. A compound according to claim 11 which is N-(3-cyclopentyloxy-4-methyloxyphenyl)- 4-pyridinecarboxamide.

13. A compound according to claim 11 which is N-(3-cyclopentyloxy-4-methyloxyphenyl)- 3,5-dichloro-4-pyridinecarboxamide.

14. A pharmaceutical composition for the prophylaxis or treatment of an unwanted inflammatory response or muscular spasm in a patient comprising, in admixture with a pharmaceutically acceptable diluent, carrier or excipient, a pharmaceutically-effective amount of a compound according to claim 1.

15. A pharmaceutical composition for the prophylaxis or treatment of an unwanted inflammatory response or muscular spasm in a patient comprising, in admixture with a pharmaceutically acceptable diluent, carrier or excipient, a pharmaceutically-effective amount of a compound according to claim 12.

16. A pharmaceutical composition for the prophylaxis or treatment of an unwanted inflammatory response or muscular spasm in a patient comprising, in admixture with a pharmaceutically acceptable diluent, carrier or excipient, a pharmaceutically-effective amount of a compound according to claim 13.

* * * * *